(12) United States Patent
Russell et al.

(10) Patent No.: US 10,806,868 B1
(45) Date of Patent: Oct. 20, 2020

(54) MESH NEBULIZER SYSTEMS

(71) Applicant: MONQ, LLC, Goodlettsville, TN (US)

(72) Inventors: Kevin Russell, West Palm Beach, FL (US); Jared Fishman, Goodlettsville, TN (US)

(73) Assignee: MONQ, LLC, Goodlettsville, TN (US)

( * ) Notice: Subject to any disclaimer, the term of this patent is extended or adjusted under 35 U.S.C. 154(b) by 0 days.

(21) Appl. No.: 16/835,760

(22) Filed: Mar. 31, 2020

Related U.S. Application Data

(60) Provisional application No. 62/988,256, filed on Mar. 11, 2020, provisional application No. 62/969,375, filed on Feb. 3, 2020.

(51) Int. Cl.
*A61M 11/00* (2006.01)
*A61M 21/00* (2006.01)
*A61M 16/00* (2006.01)
*A61M 15/00* (2006.01)

(52) U.S. Cl.
CPC ....... *A61M 11/005* (2013.01); *A61M 15/0021* (2014.02); *A61M 15/0091* (2013.01); *A61M 2016/0027* (2013.01); *A61M 2021/0016* (2013.01); *A61M 2205/0211* (2013.01); *A61M 2205/3584* (2013.01); *A61M 2205/8206* (2013.01); *A61M 2205/8237* (2013.01); *A61M 2209/10* (2013.01)

(58) Field of Classification Search
CPC ................ A61M 11/005; A61M 15/06; A61M 11/00–08; A24F 47/00; B05B 17/0607
See application file for complete search history.

(56) References Cited

U.S. PATENT DOCUMENTS

| | | | |
|---|---|---|---|
| 3,850,534 | A | 11/1974 | O'Halloran |
| 3,901,443 | A | 8/1975 | Mitsui et al. |
| 5,299,739 | A | 4/1994 | Takahashi et al. |
| (Continued) | | | |

OTHER PUBLICATIONS

Bill Hawkins et al., "Vibrating Mesh Nebulizer Reference Design", Microchip—AN2265, 2016-2017 Microchip Technology Inc., DS00002265B (Jan. 2017) pp. 1-50.

*Primary Examiner* — Timothy A Stanis
*Assistant Examiner* — Cana A Gallegos
(74) *Attorney, Agent, or Firm* — Buchanan Ingersoll & Rooney PC

(57) ABSTRACT

A nebulizer system is disclosed, and comprises a first portion and a second portion configured for selectably receiving and electrically connecting to the first portion. The first portion includes a first housing for containing fluid, a vibratable mesh which seals a first outer opening of the first housing and configured to release fluid from the first housing through the first outer opening, first electrical conductors electrically connected to the vibratable mesh, a wick arranged such that vibration of the vibratable mesh causes release of fluid from the wick, and a biasing member compressing the wick against the vibratable mesh. The second portion includes a second housing having a second outer opening, second electrical conductors for contact with the first electrical conductors, and control electronics electrically connected to the second electrical conductors and configured to control the vibratable mesh to cause fluid release from the first housing through the outer openings.

16 Claims, 8 Drawing Sheets

(56) References Cited

U.S. PATENT DOCUMENTS

| | | | |
|---|---|---|---|
| 6,546,927 | B2 | 4/2003 | Litherland et al. |
| 6,554,201 | B2 | 4/2003 | Klimowicz et al. |
| 7,199,502 | B2 | 4/2007 | Reggio |
| 7,467,786 | B2 | 12/2008 | Jae-Bong et al. |
| 7,771,642 | B2 * | 8/2010 | Power ................ A61M 11/005 264/272.11 |
| 8,539,944 | B2 | 9/2013 | Patel et al. |
| 2011/0309552 | A1 * | 12/2011 | Amirouche ....... A61M 5/16804 264/331.11 |
| 2017/0072085 | A1 * | 3/2017 | Gruenbacher .......... A61L 9/127 |
| 2017/0119059 | A1 * | 5/2017 | Zuber ................. A24F 47/008 |
| 2018/0289907 | A1 * | 10/2018 | Marmur ............ A61M 15/0003 |

* cited by examiner

MESH NEBULIZER SYSTEMS

CROSS REFERENCE TO RELATED APPLICATIONS

Figure 10:
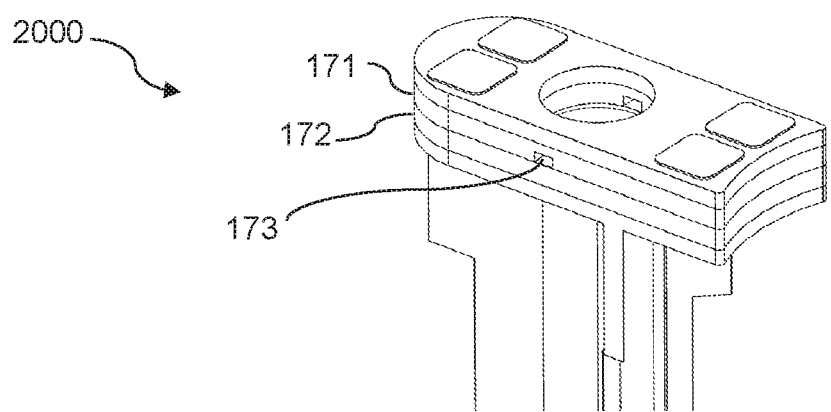

This application claims the benefit of U.S. Provisional Patent Application Ser. No. 62/969,375 filed on Feb. 3, 2020 and U.S. Provisional Patent Application Ser. No. 62/988,256 filed on Mar. 11, 2020, the entire contents of both which are incorporated herein by reference in their entireties for all purposes.

TECHNICAL FIELD

The present disclosure relates to mesh nebulizer systems, including, but not limited to, personal space nebulizer devices and inhalers.

BACKGROUND INFORMATION

A mesh nebulizer typically produces an aerosol by vibrating a mesh piezo atomizer (e.g., a piezo ceramic device), which often requires a large oscillating voltage. When such a voltage is applied at the correct frequency, the mesh oscillates to push fluid through small laser-drilled holes in the mesh.

Conventional combustion and heat-based smoking apparatuses/inhalers can pose respiratory health concerns. These concerns include the risk of inhaling dangerous ultrafine particles, as well as risks associated with high operating temperatures. Such high temperatures can chemically alter the inhaled material as well as lung tissue.

Conventional nebulizer systems typically need to be maintained in a gravity-fed, specific orientation during operation. Typical smoking products are held below the mouth for ergonomic reasons, and ultrasonic mesh nebulizers conventionally use gravity to keep fluid in contact with a nebulizing mesh. Moreover, conventional inhalers can suffer from clogging of the nebulizing mesh during inhalation, thus requiring the user to manually wipe the output area of the nebulizer.

SUMMARY

A nebulizer system is disclosed. The nebulizer system comprises a first portion and a second portion configured for selectably receiving and electrically connecting to the first portion. The first portion includes a first housing configured to contain fluid and having a first outer opening, a vibratable mesh which seals the first outer opening of the first housing and configured to release fluid from the first housing through the first outer opening, first electrical conductors electrically connected to the vibratable mesh and configured for outer electrical contact, a wick located inside the first housing and arranged such that vibration of the vibratable mesh causes release of fluid from the wick, and a biasing member compressing the wick against the vibratable mesh. The second portion includes a second housing having a second outer opening, second electrical conductors configured to contact the first electrical conductors when the first portion is received by the second portion, and control electronics electrically connected to the second electrical conductors and configured to control the vibratable mesh to cause release of fluid from the first housing through the first and second outer openings.

Another nebulizer system is disclosed. The nebulizer system comprises a first portion and a second portion configured for selectably receiving and electrically connecting to the first portion. The first portion includes a first housing configured to contain fluid and having a first outer opening, a vibratable mesh which seals the first outer opening of the first housing and configured to release fluid from the first housing through the first outer opening, first electrical conductors electrically connected to the vibratable mesh and configured for outer electrical contact, and a wick located inside the first housing and arranged such that vibration of the vibratable mesh causes release of fluid from the wick. The vibratable mesh is held between two elastic material membranes at the first outer opening. The second portion includes a second housing having a second outer opening, second electrical conductors configured to contact the first electrical conductors when the first portion is received by the second portion, and control electronics electrically connected to the second electrical conductors and configured to control the vibratable mesh to cause release of fluid from the first housing through the first and second outer openings.

A cartridge is disclosed. The cartridge comprises a housing configured to contain fluid and having an outer opening, a vibratable mesh which seals the outer opening of the housing and configured to release fluid from the housing through the outer opening, electrical conductors electrically connected to the vibratable mesh and configured for outer electrical contact, a wick located inside the first housing and arranged such that vibration of the vibratable mesh causes release of fluid from the wick, and a biasing member compressing the wick against the vibratable mesh. The vibratable mesh is held between two elastic material membranes at the outer opening.

BRIEF DESCRIPTION OF THE DRAWINGS

Other features and advantages disclosed herein will become more apparent from the following detailed description of exemplary embodiments when read in conjunction with the attached drawings.

FIG. 1 is a schematic representation of a cross-sectional view of an exemplary embodiment of a nebulizer system.

FIG. 2 is a schematic representation of a perspective view of an exemplary embodiment of a nebulizer system.

FIG. 3 is a schematic representation of another perspective view of an exemplary embodiment of a nebulizer system.

FIG. 4 is a schematic representation of another perspective view of an exemplary embodiment of a nebulizer system, with housing components removed.

FIG. 5 is a schematic representation of a perspective view of an exemplary embodiment of a first portion or cartridge, with housing elements removed.

FIG. 6 is a schematic representation of a perspective view of an exemplary embodiment of a first portion or cartridge, with additional components removed.

FIG. 7 is a schematic representation of a perspective view of an exemplary embodiment of a first portion or cartridge, with additional components removed.

FIG. 8 is a schematic representation of the top portion of aside cross-sectional view of an exemplary embodiment of a nebulizer system for inhaling applications.

FIG. 9 is a schematic representation of atop cross-sectional view of an exemplary embodiment of a nebulizer system for inhaling applications.

FIG. 10 is a schematic representation of a perspective view of an exemplary embodiment of a first portion or cartridge for inhaling applications, with housing elements removed.

Figure 11:
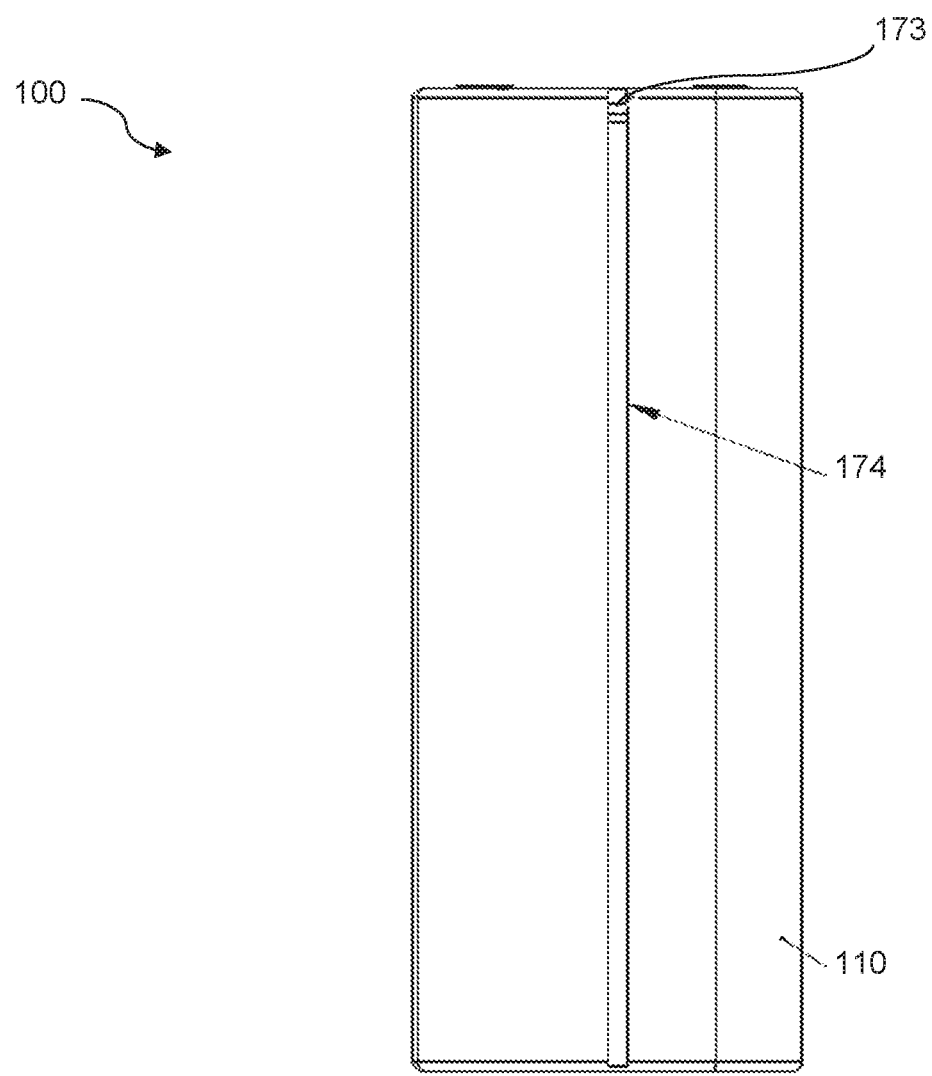

FIG. 11 is a schematic representation of a side view of an exemplary embodiment of a first portion or cartridge for inhaling applications.

DETAILED DESCRIPTION

Exemplary embodiments disclosed herein can provide a portable nebulizer (e.g., ultrasonic) with an advantageous cartridge system with possible applications in, but not limited to, aromatherapy, recreational use, and respiratory medicine. Disclosed exemplary embodiments can also provide a small form factor product. Clogging issues associated with conventional inhalers are also addressed by a self-cleaning design in disclosed exemplary embodiments.

In aromatherapy applications, exemplary embodiments may provide a portable device that produces aroma on demand, with different removable cartridges for different scents.

In recreational use applications, exemplary embodiments may involve a healthier use of nicotine/THC products involving lower-temperature systems. The choice of material, with customized scents or tastes, may also be an advantage.

From the perspective of respiratory medicine, exemplary embodiments may involve more targeted formulation whereby only a specific material is inhaled, more targeted particle size whereby nebulizers can target a specific particle size thereby reducing or eliminating the risk of ultrafine particles, and lower heat application whereby the effects of temperature on chemical compounds can be mitigated. Exemplary embodiments may also not involve vaporizing, and thus may provide a safer environment for the user.

Figure 1:
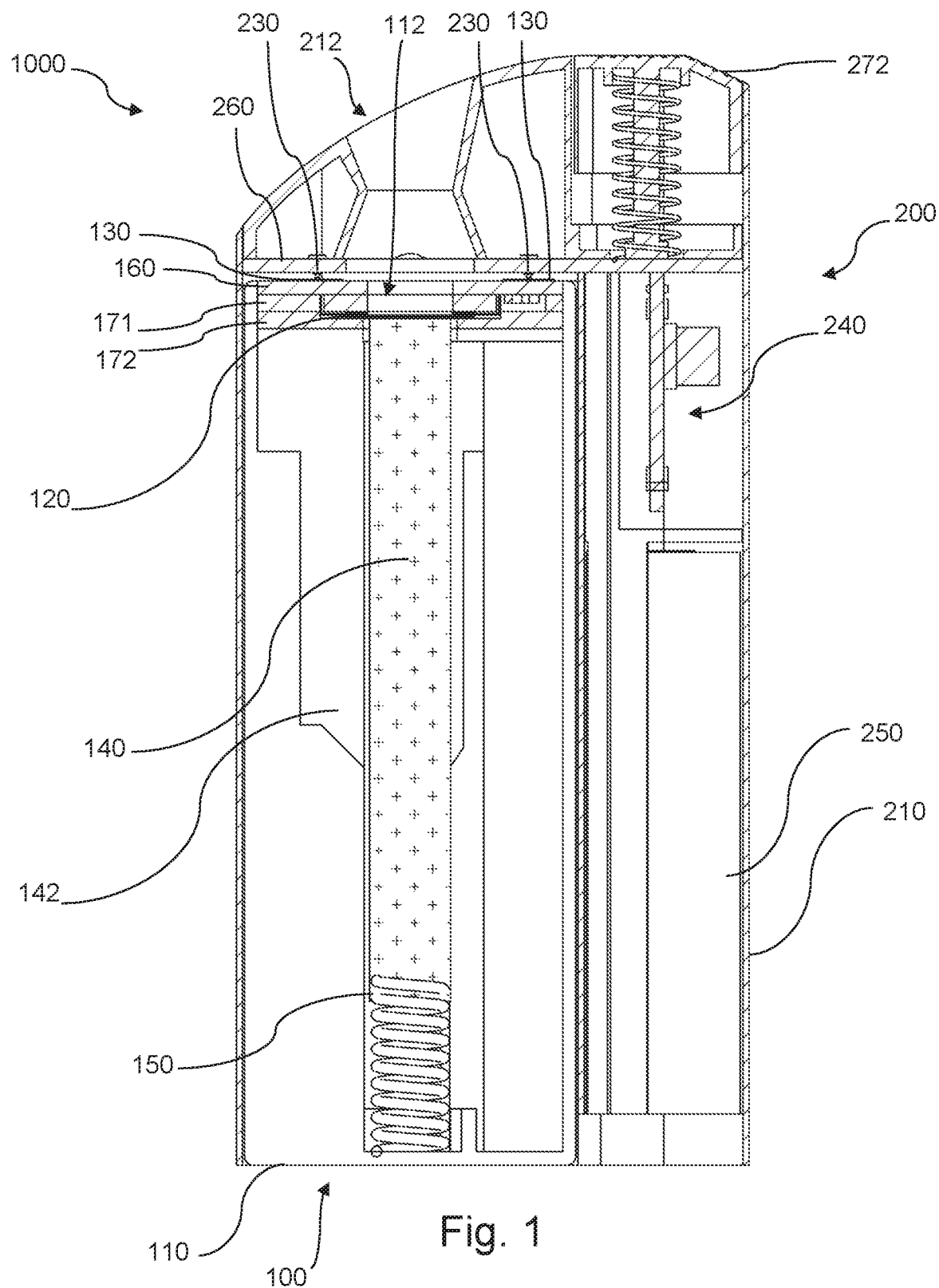
Figure 2:
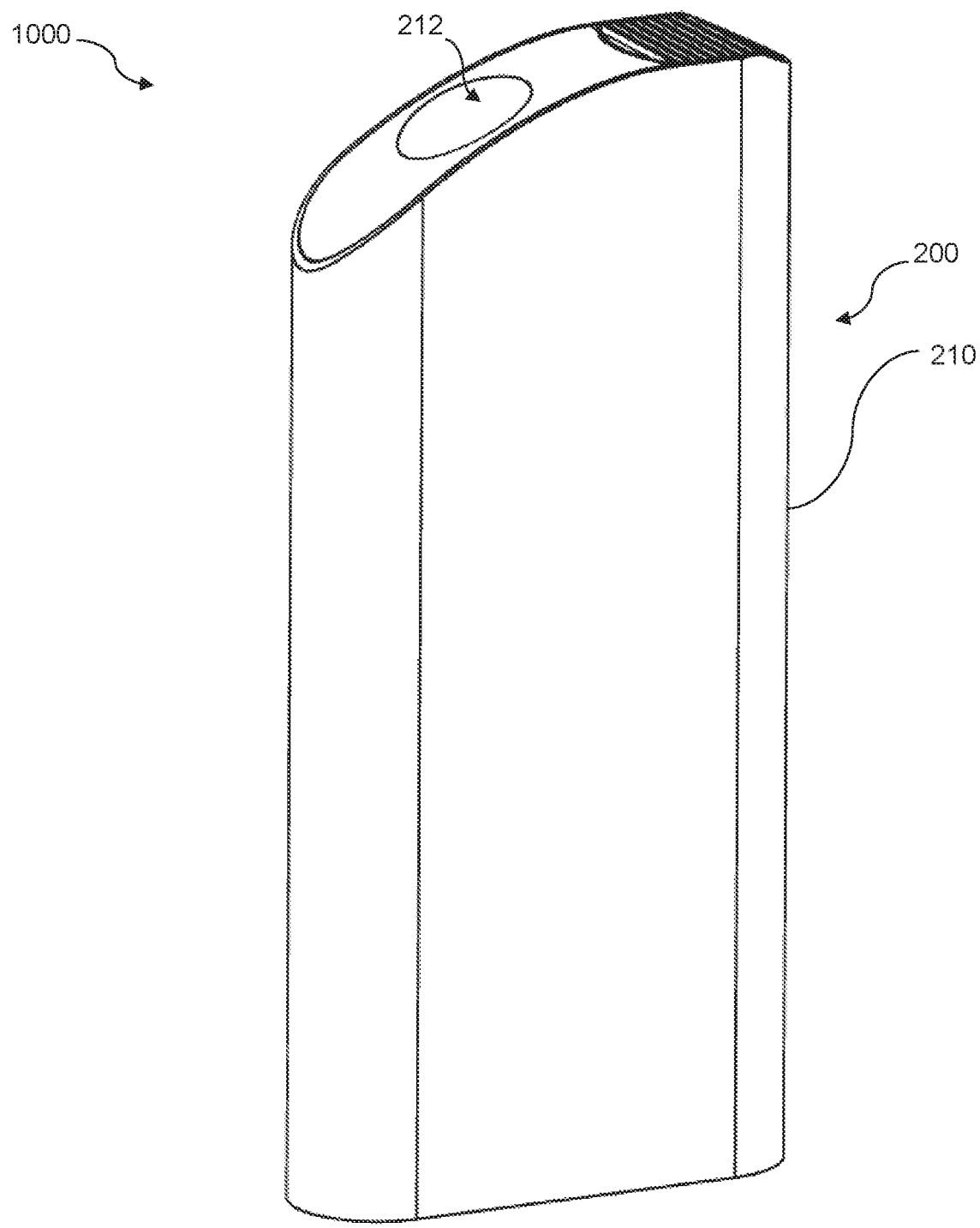
Figure 3:
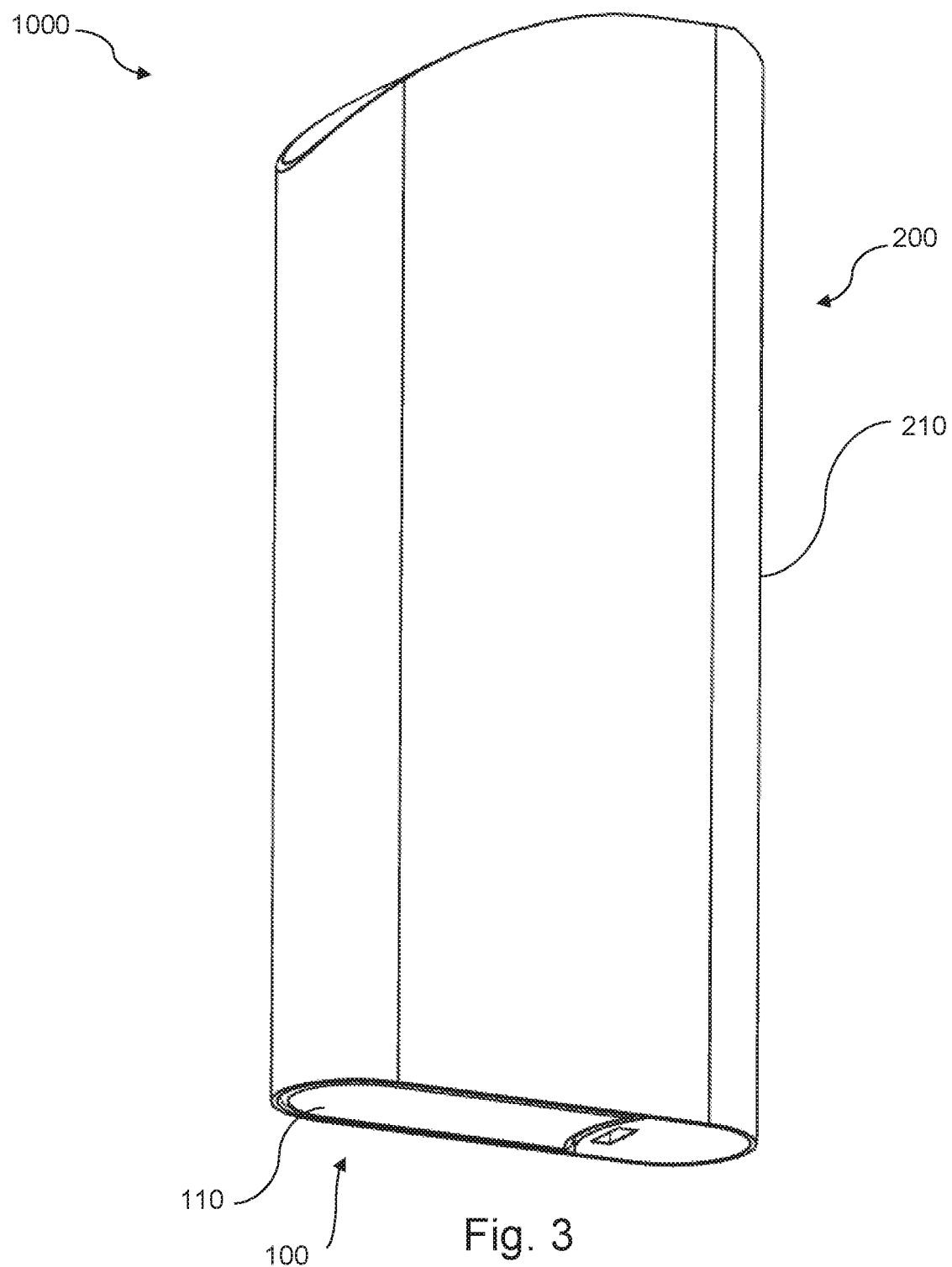
Figure 4:
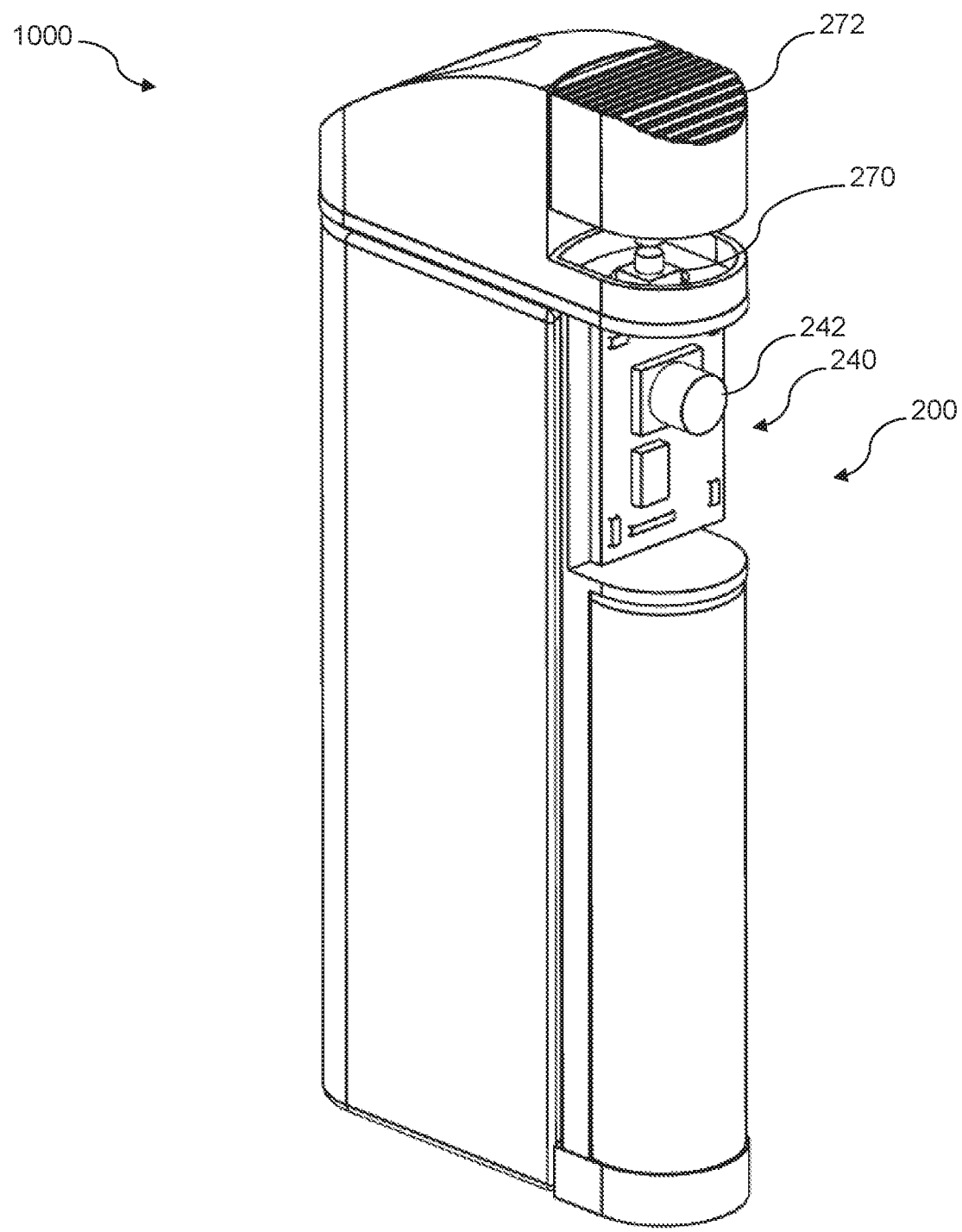
Figure 5:
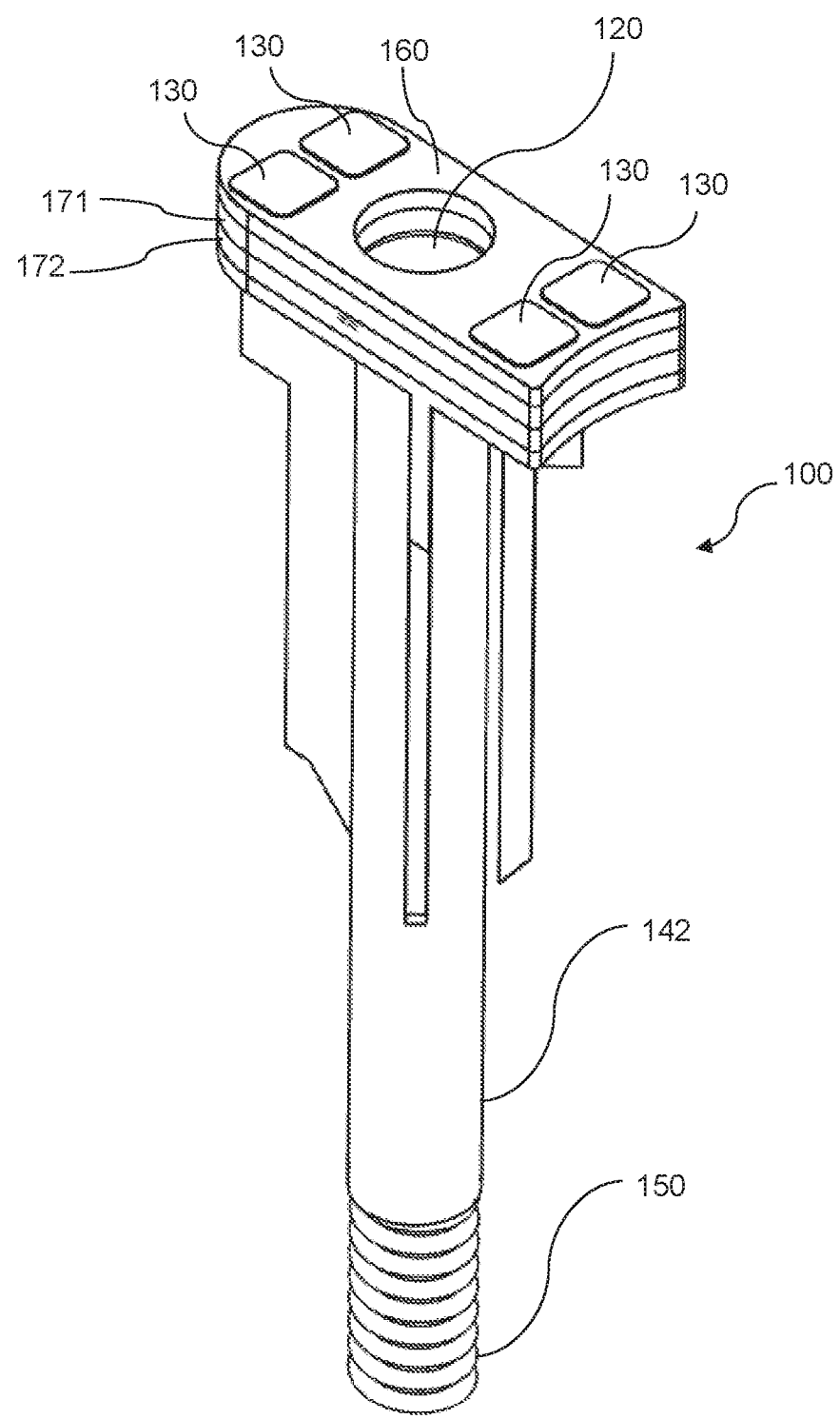
Figure 6:
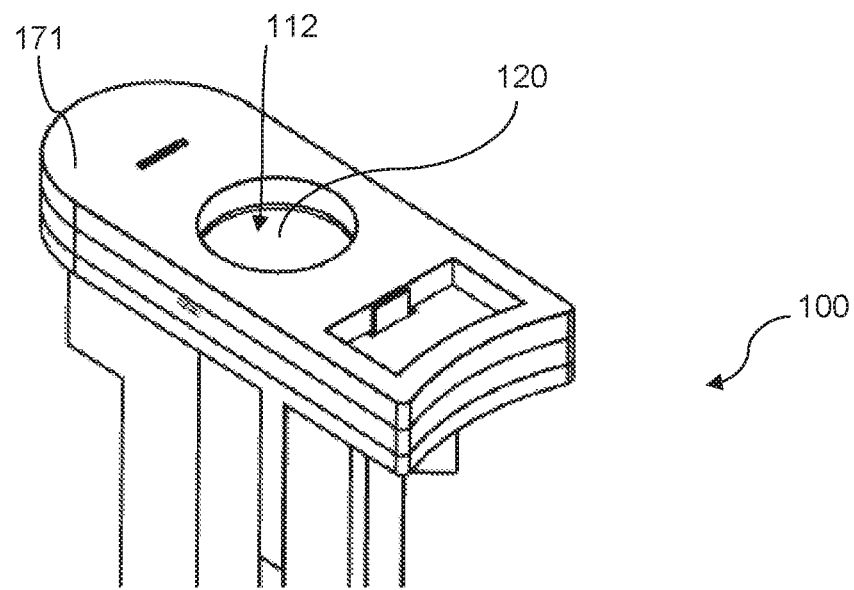
Figure 7:
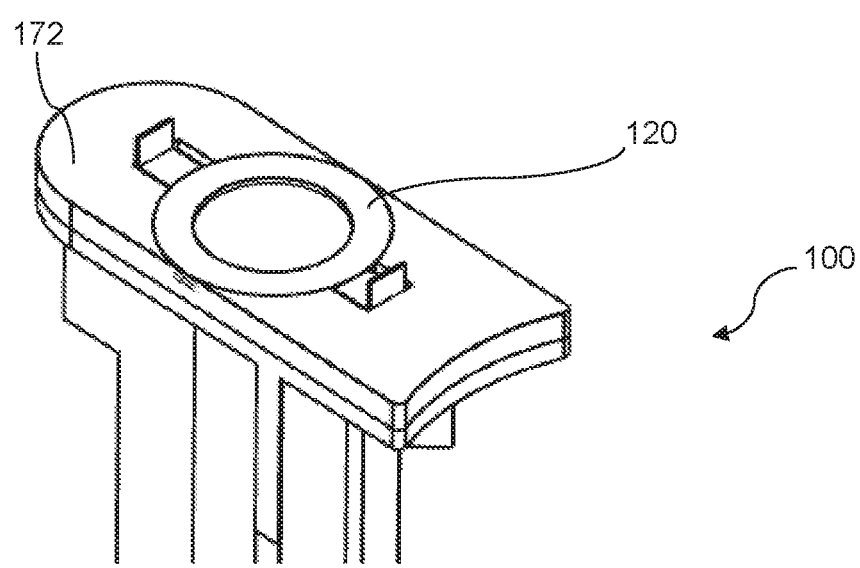
Figure 8:
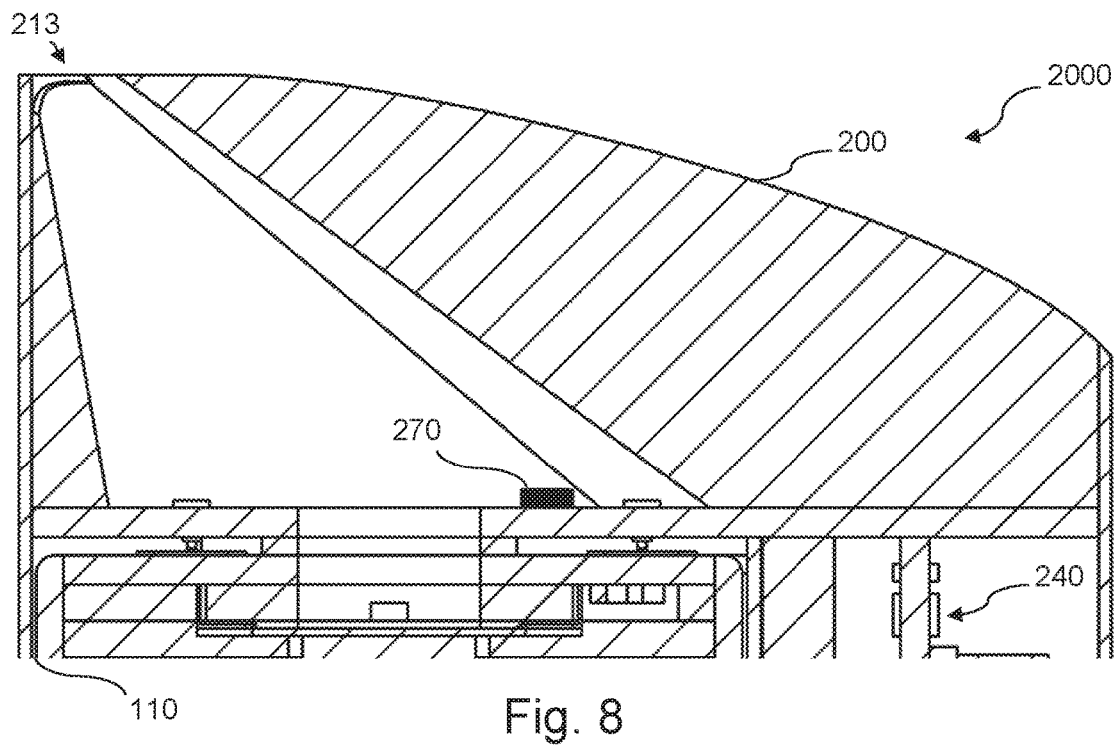
Figure 9:
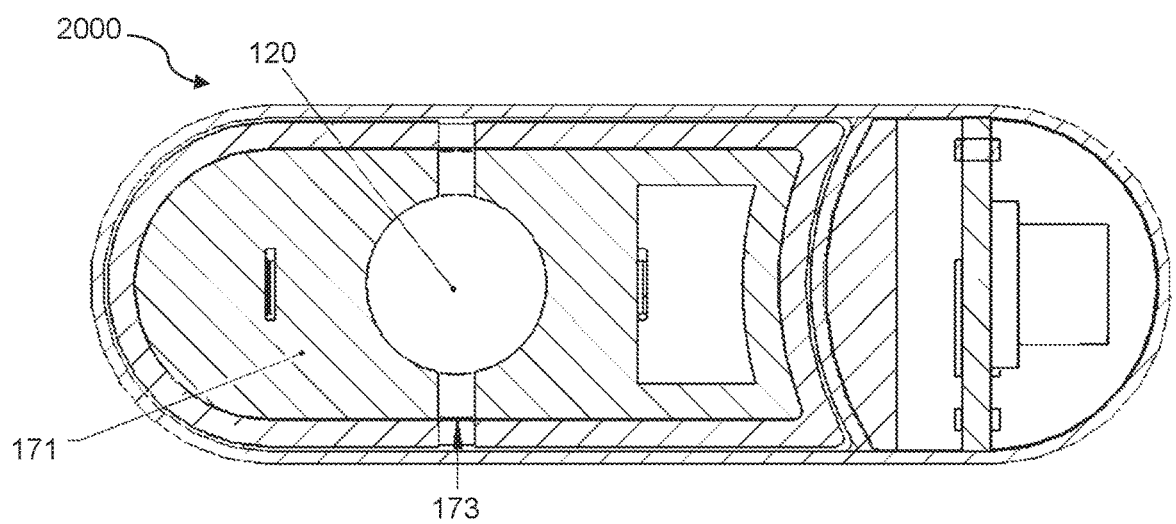

FIGS. 1-4 show an exemplary embodiment of a nebulizer system 1000 comprising a first portion 100 and a second portion 200. In FIG. 4, housing components were removed to expose interior components for illustrative purposes. FIGS. 5-7 show an exemplary embodiment of a first portion 100, in which various components were removed as well for illustrative purposes.

In exemplary embodiments, the first portion 100 includes a first housing 110, a vibratable mesh 120, first electrical conductors 130, a wick 140 and a biasing member 150. The first housing 110 is configured to contain fluid, and has a first outer opening 112. The vibratable mesh 120 seals the first outer opening 112 of the first housing 110, and is configured to release fluid from the first housing 110 through the first outer opening 112. The first electrical conductors 130 are electrically connected to the vibratable mesh 120 and are configured for outer electrical contact. The wick 140 is located inside the first housing 110, and is arranged such that vibration of the vibratable mesh 120 causes release of fluid from the wick 140. The biasing member 150 compresses the wick 140 against the vibratable mesh 120. The first housing 110 may be configured to contain fluid by, for example, being configured to directly contain fluid, or, for example, by housing a fluid container.

In exemplary embodiments, the second portion 200 is configured for selectably receiving and electrically connecting to the first portion 100, and includes a second housing 210 having a second outer opening 212, second electrical conductors 230, and control electronics 240. The second electrical conductors 230 are configured to contact the first electrical conductors 130 when the first portion 100 is received by the second portion 200. The control electronics 240 are electrically connected to the second electrical conductors 230, and are configured to control the vibratable mesh 120 to cause release of fluid from the first housing 110 through the first and second outer openings 112, 212.

In exemplary embodiments, the vibratable mesh 120 diameter, vibratable mesh 120 frequency, and the size of the first outer opening 112 are selected based on the fluid to be contained in the first housing 110 (e.g., based on fluid viscosity). In exemplary embodiments, by providing the vibratable mesh 120 in the first portion 100 which contains the fluid, the mesh can be tailored to the material being atomized or otherwise output.

In exemplary embodiments, the wick 140, assisted by the biasing member 150, can advantageously carry working fluid vertically against gravity. The sealed first housing 110 further permits tilting of the first portion 100 while reducing the risk of leakage from the region of the vibratable mesh 120. As such, exemplary embodiments of the disclosed first portion 100 containing the fluid, the vibratable mesh 120 sealed to the first housing 110, and a wick 140 can advantageously output nebulized fluid in any orientation of the system, including an upside-down orientation.

In exemplary embodiments, the wick 140 is held inside the first housing 110 by a wick retaining feature 142.

In exemplary embodiments, the biasing member 150 can be a spring, such as, but limited to, a coil spring, or any other suitable biasing element. The biasing member 150 is configured to ensure desirable pressure on the wick 140 and vibratable mesh 120.

In exemplary embodiments, the second outer opening 212 is located at the top of the nebulizer system 1000.

In exemplary embodiments, the control electronics 240 include a power capacitor 242 configured to store high voltage energy, and an oscillating or resonant circuit configured to output oscillation voltage to the vibratable mesh 120, in order to cause vibration of the vibratable mesh 120.

In exemplary embodiments, the wick 140 is circular cylindrical. The wick 140 can alternatively be of any other suitable shape. The wick 140 has desired capillary properties, such that the vertical fluid flow delivery of the wick 140 is greater than or equal to the volumetric flow of nebulizer system 1000. In exemplary embodiments, the biasing member 150 assists the wick 140 in vertically carrying sufficient amounts of fluid.

In exemplary embodiments, the second outer opening 212 includes a nozzle configured to direct fluid flow in a desirable direction.

In exemplary embodiments, the first electrical conductors 130 are configured to receive high-voltage (e.g., but not limited to 50-200 Volts, or more than 100 Volts) signals to drive the vibratable mesh 120.

In exemplary embodiments, the first portion 100 includes a first interface printed circuit board 160 which includes or supports the first electrical conductors 130.

In exemplary embodiments, the first interface printed circuit board 160 further includes low-voltage digital electronics that store information, such as a memory chip containing information about the fluid contained in the first housing 110.

In exemplary embodiments, the second portion 200 includes a second interface printed circuit board 260 which includes or supports the second electrical conductors 230.

In exemplary embodiments, the first and/or second electrical conductors 130, 230 include compressive electrical connectors.

In exemplary embodiments, compressive electrical connectors facilitate desired contact between electrical components of the first and second portions 100, 200. In exemplary embodiments, the first and/or second electrical conductors 130, 230 include conducting plates, pogo pins or spring-loaded pins. In alternative exemplary embodiments, the first and/or second electrical conductors 130, 230 can include any other electrical connector.

In exemplary embodiments, the vibratable mesh 120 is a piezo-ceramic element. In alternative exemplary embodiments, the vibratable mesh 120 can be any other electrically activated nebulizing device, preferably a low-temperature electrically activated nebulizing device.

In exemplary embodiments, the second portion 200 further comprises a power source 250 electrically connected to and providing electrical power to the control electronics 240. The power source 250 can include, but is not limited to, a single-use battery, a rechargeable battery, and/or a power adapter for connection to an external power supply. Preferably, the power source 250 is located at the bottom of the nebulizer system 1000 for desired weight distribution. In exemplary embodiments, placing a battery 250 and a cartridge/first portion 100 on opposite sides of the system can advantageously result in a small form factor device.

In exemplary embodiments, a battery (e.g., a lithium battery providing 3.7-4.2 Volts) is used, and a single or multistage boost circuit is implemented. For example, a first stage can provide 50 Volts, while a second stage can provide additional amplification, and additionally can provide voltage oscillation. In exemplary embodiments, such a configuration may provide a power efficiency of 85%-90%. In exemplary embodiments, using excess heat generated from the electrical amplification process, fluid viscosity can be reduced (e.g., by up to 10 times). Positioning of the power source 250 along the fluid housing 110 allows for transmission of this excess heat into the fluid for viscosity reduction. Since nebulizing meshes typically have an upper limit to the viscosity of the fluid it can atomize, this can allow for a wider variety of fluids to be used, and possibly more dense products.

In exemplary embodiments, the vibratable mesh 120 is held between two elastic material membranes 171, 172 at the first outer opening 112. These elastic material membranes 171, 172 are visible in the cross-sectional schematic view of FIG. 1, as well as the partial views of FIGS. 5-7. Alternatively, other sealing mechanisms can be used to seal the vibratable mesh 120 at the first outer opening 112, e.g., a single overmolded elastic membrane, or any other suitable sealing arrangement.

In exemplary embodiments, this dual seal design 171, 172 can help keep the vibratable mesh 120 sealed to reduce risk of, or prevent, leakage when the first portion 100 or nebulizer system 1000 is held upside-down. Such an arrangement can also help protect electrical components from fluid interference.

In exemplary embodiments, the first housing 110 can be recharged with fluid, for example by puncturing a pierceable membrane (not shown).

In exemplary embodiments, the nebulizer system 1000 further comprises actuator electronics 270 electrically connected to, or integral with, the control electronics 240, and configured, upon activation, to trigger release of fluid from the first housing 110. In exemplary embodiments, the actuator electronics can reside in the first portion 100 or in the second portion 200.

In exemplary embodiments, the second portion 200 includes an actuator surface 272 configured to be pressed by a user to cause activation of the actuator electronics 270. In exemplary embodiments, the actuator surface 272 can reside in the first portion 100 or in the second portion 200. The actuator surface 272 can be, for example, the surface of an external button. Alternatively or additionally, the actuator electronics 270 can include a pressure sensor.

In exemplary embodiments, the second portion 200 includes securing/ejection feature(s) (not shown) for retaining and selectively allowing ejection of the first portion 100. Securing/ejection feature(s) include, but may not be limited to, a snap fit arrangement. This can help provide a convenient and user-friendly cartridge-like configuration.

In an alternative inhaler embodiment, fluid redirecting elements direct air flow along (i.e., crossflow), or at an angle relative to, the vibratable mesh 120. In exemplary embodiments in which airflow is directed at an angle relative to the vibratable mesh 120, a jet of air that impinges on the surface of the vibratable mesh 120 is therefore generated. The jet created by a nozzle can clear clogs due to excess viscosity. This can reduce the risk of, or prevent, fluid accumulation at the vibratable mesh 120 (e.g., at the top of the vibratable mesh 120) as a user inhales. This can provide an advantageous self-cleaning device.

FIGS. 8-11 illustrate an exemplary embodiment of a nebulizer system 2000 for inhaling applications. Notwithstanding the exemplary components specifically described below with respect to FIGS. 8-11, this exemplary embodiment 2000 can include essentially the same components as the exemplary embodiment 1000 shown in FIG. 1.

The exemplary embodiment of a nebulizer shown in FIG. 8 includes a second portion 200 having a nozzle with an ergonomic mouthpiece 213 designed to fit comfortably when inhaling. Interior surfaces of the nozzle can be hydrophobic in order to reduce the risk of, or prevent, fluid build-up inside the nozzle. Alternatively or additionally, the interior surfaces of the nozzle may be angled to reduce the risk of, or prevent, fluid deposits.

An exemplary embodiment of a nebulizer system 2000 further includes actuator electronics 270 including a pressure sensor configured to detect when the user is inhaling through the mouthpiece. Upon such detection, the actuator electronics 270 are configured to trigger release of fluid from the first housing 110.

As shown in the exemplary embodiment of FIGS. 9 and 10, at least one of the elastic material membranes 171, 172 can include one or more airflow channels 173 to allow air to travel between the seals. This airflow can be powered by the user's inhalation. A channel 173 can extend from an outer surface of the elastic material membrane 171, 172 to the vibratable mesh 120. The channels 173 can be horizontal, and can thus extend parallel to a main plane of the vibratable mesh 120. These channels 173 can act as directional nozzles, which accelerate flow velocity and provide cleaning action to the vibratable mesh 120. In exemplary embodiments, the airflow channel arrangement may be asymmetrical, cylindrical, horizontal or vertical. In exemplary embodiments, if clogging is too large, these channels can act as a clog removal or overflow mitigation mechanism. Although the illustrated embodiments show channels 173 creating crossflow along the vibratable mesh 120, such channels 173 can be arranged at an angle relative to the main plane of the vibratable mesh 120 to create flow that impinges on the vibratable mesh 120.

As shown in the exemplary embodiment of FIG. 11, vertical airflow channels 174 can connect with horizontal flow channels 173 to help direct air to the vibratable mesh plane. In exemplary embodiments, such vertical airflow channels 174 can include small-diameter pipes in the first housing 110 of the first portion 100, or surface features of the first housing 110.

Exemplary embodiments of nebulizer systems disclosed herein can provide inhaler solutions functioning at lower, and thus safer, temperatures than conventional vaping apparatuses.

Exemplary embodiments of nebulizer systems disclosed herein can be integrated with a power level sensor, a fluid level sensor, and/or other sensors, and with wireless or wired communication module(s) (e.g., BLUETOOTH or other wired or wireless protocols) for interfacing with software (e.g., a mobile application or other computer software) for monitoring power levels, fluid levels, etc. A memory chip can also be integrated in the first portion 100 for storing information regarding the fluid contained in the first housing 110, accessible by said software.

Exemplary embodiments of nebulizer systems are also equipped with a backlight positioned near or at the second outer opening 212, to facilitate visibility of the mist in extreme lighting conditions. This backlight can also act as a device indicator.

It will be appreciated by those skilled in the art that the disclosure herein can be embodied in other specific forms without departing from the spirit or essential characteristics thereof. The presently-disclosed embodiments are therefore considered in all respects to be exemplary and not restricted. The scope of the invention is indicated by the appended claims rather than the foregoing description and all changes that come within the meaning and range and equivalence thereof are intended to be embraced therein.

What is claimed is:

1. A nebulizer system comprising:
   (i) a first portion including:
      a first housing configured to contain fluid and having a first outer opening,
      a vibratable mesh sealing the first outer opening of the first housing and configured to release fluid from the first housing through the first outer opening, wherein the vibratable mesh is held between two elastic material membranes at the first outer opening, and at least one of the two elastic material membranes includes at least one air flow channel extending from an outer surface of the at least one of the two elastic material membranes to the vibratable mesh,
      first electrical conductors electrically connected to the vibratable mesh and configured for outer electrical contact,
      a wick located inside the first housing and arranged such that vibration of the vibratable mesh causes release of fluid from the wick, and
      a biasing member compressing the wick against the vibratable mesh; and
   (ii) a second portion configured for selectably receiving and electrically connecting to the first portion, the second portion including:
      a second housing having a second outer opening,
      second electrical conductors configured to contact the first electrical conductors when the first portion is received by the second portion, and
      control electronics electrically connected to the second electrical conductors and configured to control the vibratable mesh to cause release of fluid from the first housing through the first and second outer openings.

2. The nebulizer system of claim 1, wherein the first portion includes a first interface printed circuit board which includes or supports the first electrical conductors.

3. The nebulizer system of claim 1, wherein the second portion includes a second interface printed circuit board which includes or supports the second electrical conductors.

4. The nebulizer system of claim 1, wherein the biasing member is a coil spring.

5. The nebulizer system of claim 1, wherein the first and/or second electrical conductors include compressive electrical connectors.

6. The nebulizer system of claim 1, wherein the vibratable mesh is a piezo-ceramic element.

7. The nebulizer system of claim 1, wherein the second portion further comprises a power source electrically connected to and providing electrical power to the control electronics.

8. The nebulizer system of claim 1, wherein the at least one air flow channel extends parallel to a main plane of the vibratable mesh.

9. The nebulizer system of claim 1, wherein the at least one air flow channel extends at an angle relative to a main plane of the vibratable mesh.

10. The nebulizer system of claim 1, wherein the at least one air flow channel is at least one first air flow channel, and the first housing includes at least one second air flow channel extending vertically to the at least one first air flow channel either along an outer surface of the first housing or within the first housing.

11. The nebulizer system of claim 1, further comprising actuator electronics electrically connected to, or integral with, the control electronics, and configured, upon activation, to trigger release of fluid from the first housing.

12. The nebulizer system of claim 11, wherein the second portion includes an actuator surface configured to be pressed by a user to cause activation of the actuator electronics.

13. The nebulizer system of claim 11, wherein the actuator electronics include a pressure sensor configured to detect air flow through a nozzle of the second portion.

14. The nebulizer system of claim 1, wherein the second portion includes a nozzle having a hydrophobic interior surface.

15. A nebulizer system comprising:
   (i) a first portion including:
      a first housing configured to contain fluid and having a first outer opening,
      a vibratable mesh held between two elastic material membranes at the first outer opening, sealing the first outer opening, and configured to release fluid from the first housing through the first outer opening, wherein at least one of the two elastic material membranes includes at least one air flow channel extending from an outer surface of the at least one of the two elastic material membranes to the vibratable mesh,
      first electrical conductors electrically connected to the vibratable mesh and configured for outer electrical contact, and
      a wick located inside the first housing and arranged such that vibration of the vibratable mesh causes release of fluid from the wick; and
   (ii) a second portion configured for selectably receiving and electrically connecting to the first portion, the second portion including:
      a second housing having a second outer opening,
      second electrical conductors configured to contact the first electrical conductors when the first portion is received by the second portion, and
      control electronics electrically connected to the second electrical conductors and configured to control the vibratable mesh to cause release of fluid from the first housing through the first and second outer openings.

16. The nebulizer system of claim 15, wherein the at least one air flow channel extends parallel to a main plane of the vibratable mesh.

* * * * *